United States Patent [19]

Robin

[11] Patent Number: 4,697,014
[45] Date of Patent: Sep. 29, 1987

[54] CATALYTIC PARTIAL CYCLOTRIMERIZATION OF POLYISOCYANATES AND PRODUCT THEREOF

[75] Inventor: Jean Robin, Lyons, France

[73] Assignee: Rhone-Poulenc Specialites Chimiques, Courbevoie, France

[21] Appl. No.: 843,512

[22] Filed: Mar. 25, 1986

[30] Foreign Application Priority Data

Mar. 25, 1985 [FR] France ................... 85 04608

[51] Int. Cl.$^4$ ............ C07D 251/34; C08G 18/02; C08F 4/16
[52] U.S. Cl. ................... 544/193; 544/222; 521/128; 521/902; 528/52; 526/194
[58] Field of Search .............. 544/193, 222; 521/128, 521/902; 528/52; 526/194

[56] References Cited

U.S. PATENT DOCUMENTS 4,412,073 10/1983 Robin ................... 544/193
4,537,961 8/1985 Robin ................... 544/193

OTHER PUBLICATIONS

Robin, Abstract E.P. 89,297 (see U.S. Pat. No. 4,537,961 for complete English translation) 9/21/83.

Primary Examiner—Henry R. Jiles
Assistant Examiner—J. G. Mullins
Attorney, Agent, or Firm—Burns, Doane, Swecker & Mathis

[57] ABSTRACT

Storage-stable polyisocyanurate-polyisocyanates, essentially devoid of polyisocyanate monomer and dimer over time, are conveniently prepared by catalytically cyclotrimerizing an aliphatic, cycloaliphatic or aromatic polyisocyanate in the presence of a catalytically effective amount of an aminosilyl catalyst, and terminating the cyclotrimerization reaction when predetermined desired amount of isocyanurate group has been reached, by adding to the reaction mixture a reaction terminating amount of water.

14 Claims, No Drawings

CATALYTIC PARTIAL CYCLOTRIMERIZATION OF POLYISOCYANATES AND PRODUCT THEREOF

BACKGROUND OF THE INVENTION

1. Field of the Invention

The present invention relates to an improved process for the preparation of polyisocyanurate-polyisocyanates, by partial catalytic cyclotrimerization of polyisocyanates, the subject reaction ultimately and deliberately being stopped or terminated when the trimer content reaches the predetermined and desired value. More especially, the present invention essentially relates to an improved process for deactivating the catalyst employed therein, said catalyst comprising an aminosilyl compound.

2. Description of the Prior Art

In my U.S. Pat. No. 4,412,073, assigned to the assignee hereof, a process is described for the preparation of monomeric or polymeric compounds containing isocyanurate groups, and especially of polyisocyanurate-polyisocyanates, by catalytic cyclotrimerization of aliphatic or alicyclic isocyanates in the presence of catalytically effective amounts of compounds containing one or more aminosilyl group(s). More particularly, said '073 patent describes a process for preparing polyisocyanurate-polyisocyanates by partial catalytic cyclotrimerization of polyisocyanates, especially of aliphatic or alicyclic diisocyanates; in this case, the cyclotrimerization reaction is stopped when the isocyanurate group content reaches the required value, by deactivating the aminosilylated catalyst. Various means for deactivating the catalyst have been proposed. Thus, in the aforesaid '073 patent such catalyst deactivation results via the destruction thereof by means of an acidic compound (hydrochloric acid, acid chloride) which is added to the reaction mixture. And in my U.S. Pat. No. 4,537,961, also assigned to the assignee hereof, the catalyst is destroyed or consumed by the addition of an organic compound containing at least one hydroxyl group to the reaction medium, such as enols, alcohols, phenols, oximes, or compounds containing one or more hydroxysilyl group(s), or of a compound produced by the reaction of a hydroxylated compound of this type with a reactant containing one or more isocyanate group(s), such as carbamates, which may be produced in situ by the reaction of a hydroxylated compound with excess diisocyanate, under conditions employed for the addition of the hydroxylated compound. After the reaction has been stopped, the excess diisocyanate is separated from the polyisocyanuratepolyisocyanate by distillation.

It has, however, been found that, during storage, the products obtained in this manner can sometimes give rise to free diisocyanates, which interfere with the use of the polyisocyanurate-polyisocyanates in coating compositions and especially in varnishes.

SUMMARY OF THE INVENTION

Accordingly, a major object of the present invention is the provision of an improved process for the short-stopping of the known partial catalytic cyclotrimerization of polyisocyanates, and which improved process is much simpler and more effective in respect of the storage stability of the resultant polyisocyanurate-polyisocyanates produced by partial catalytic cyclotrimerization of aliphatic, alicyclic or aromatic polyisocyanates.

More specifically, a primary attribute of the present invention is a process for blocking the cyclotrimerization reaction which is simpler than those processes heretofore known to this art.

A second attribute of the present invention is a process for blocking cyclotrimerization which results in polyisocyanurate-polyisocyanates having improved storage stability. This storage stability is reflected in the reduced likelihood that the product polyisocyanurate-polyisocyanates will evolve into a monomeric diisocyanate during storage and even when they are heated to a temperature of 60° or more for a prolonged period of time.

Briefly, the present invention features a process for the preparation of polyisocyanurate-polyisocyanates by catalytic cyclotrimerization of polyisocyanates, employing catalytically effective amounts of aminosilylated catalysts, followed, when the desired isocyanurate group content has been attained, by destruction of the catalyst by the addition of a deactivating compound to the reaction medium, and characteristically wherein water is used as the deactivator.

DETAILED DESCRIPTION OF THE PREFERRED EMBODIMENTS OF THE INVENTION

More particularly according to the present invention, it has now unexpectedly and surprisingly been found that water can be used to destroy the catalyst without damaging the polyisocyanurate-polyisocyanate. In this respect, it will of course be appreciated that the ease with which water reacts with isocyanates had motivated those skilled in this art to discount same in favor of less active hydroxylated compounds.

The amount of water can vary over wide limits; in general, however, there is no need to use more than 1 mole of water per Si-N group present in the catalyst. More specifically, the amount of water advantageously ranges from 0.25 to 1 mole per aminosilyl group, and preferably from 0.4 to 0.8 mole per aminosilyl group.

The temperature at which the water is added advantageously ranges from 0° to 100° C. It could be higher than 100° C., but this would not result in any special advantage and would entail operating under pressure. The temperature at which the water is added preferably ranges from 15° to 60° C.

The aminosilyl compounds used as cyclotrimerization catalysts in the process according to the invention are preferably those described and enumerated in my said U.S. Pat. No. 4,412,073, namely, compounds which have the formula (I):

wherein R is a monovalent radical of the hydrocarbon type, notably saturated or unsaturated aliphatic and alicyclic radicals, or aryl, aralkyl or alkylaryl radicals, optionally substituted by one or more halogen atoms or CN groups, with the proviso that two radicals R may together form a single divalent hydrocarbon radical; R' is a monovalent radical selected from among the radicals R, $SiR_3$, or amide radicals of the formula:

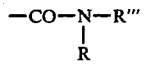

in which R''' is R or SiR$_3$, with R being as above defined, with the proviso that R', when it is not an amide group or an SiR$_3$ group, may together form with R'' a single divalent hydrocarbon radical; R'' is a monovalent radical R, or a hydrogen atom when R' is not an amide radical; and n is an integer equal to 1 or 2, with the proviso that when n is equal to 2, R' is a radical R.

The catalyst having the formula (I), which may be an aminosilane, a diaminosilane, a silylurea or a silazane, is preferably one in which R is an alkyl, alkenyl or haloalkyl or haloalkenyl radical containing from 1 to 5 carbon atoms and containing 1 to 6 chlorine and/or fluorine atoms, a cycloalkyl, cycloalkenyl or halocycloalkyl or halocycloalkenyl radical containing from 3 to 8 carbon atom and containing from 1 to 4 chlorine and/or fluorine atoms; an aryl, alkylaryl or haloaryl radical containing from 6 to 8 carbon atoms and containing from 1 to 4 chlorine and/or fluorine atoms, or a cyanoalkyl radical containing 3 to 4 carbon atoms, with the proviso that two radicals R borne by the same silicon atom may together form a single divalent radical containing from 1 to 4 carbon atoms; R' is a monovalent radical selected from among the radicals R, SiR$_3$, and CO(NR)-R''', with R''' being R or SiR$_3$, and R being as above defined, with the proviso that R' may with R'' together form an alkylene radical containing from 4 to 6 carbon atoms; R'' is an alkyl or alkenyl radical containing from 1 to 4 carbon atoms, a cycloalkyl or cycloalkenyl radical containing from 4 to 6 ring carbon atoms, a phenyl or tolyl or xylyl radical, or a hydrogen atom when R' is not an amide group.

The aminosilyl compounds of the formula (I) which are particularly preferred as cyclotrimerization catalysts are those in which R is a methyl, ethyl, propyl, vinyl or phenyl radical, optionally chlorinated and/or fluorinated; R' is a methyl, ethyl, propyl or butyl radical, an SiR$_3$ radical, with R being as above defined, or a carbonamide radical selected from among those of the formulae:

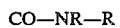

wherein R is as above defined; and R'' is a methyl, ethyl, propyl or butyl radical, or a hydrogen atom, and with the proviso that R' and R'' may together form a butylene or pentylene radical.

As aforesaid, the cyclotrimerization catalyst may be an aminosilane, a diaminosilane, a monosilylurea, a disilylurea or a silazane. The precise chemical nature of the various aminosilyl group compounds which may be used can be readily determined, given the various definitions given above for the various radicals R, R', R'' and R'''. In particular, it will be noted that the use of silylurea, obtained by the reaction of a secondary amine with N-silylisocyanates, is not envisaged. These silylureas are unsuitable for the catalytic cyclotrimerization process of the invention, since they release the silylisocyanate when heated.

The compound containing an aminosilyl group will be an aminosilane when n is equal to 1 and when R' denotes a radical R, with the radicals R and R'' being as above defined, and again with the proviso that two radicals R may together form a single divalent radical, or else R' and R'' may themselves together form a single divalent radical. Exemplary of the aminosilanes, the following are representative:

(i) Methylaminotrimethylsilane;
(ii) Dimethylaminotrimethylsilane;
(iii) Diethylaminotrimethylsilane;
(iv) Dibutylaminotrimethylsilane;
(v) Diethylaminodimethylvinylsilane; and
(vi) Diethylaminodimethylphenylsilane.

The compound containing an aminosilyl group will be a diaminosilane when n is equal to 2 and when R' denotes the radical R, with the radicals R and R'' being as above defined, and again with the proviso that two radicals R may together form a single divalent radical, or else R' and R'' may themselves together form a single divalent radical. Exemplary of the diaminosilanes, the following are representative:

(i) Bis(dimethylamino)dimethylsilane;
(ii) Bis(dimethylamino)dimethylsilane;
(iii) Bis(dibutylamino)dimethylsilane; and
(iv) Bis(dimethylamino)methylphenylsilane.

The compound containing an aminosilyl group will be a silylurea when n is equal to 1 and when R' denotes the carbonamide group

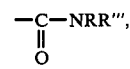

in which R''' denotes a radical R or SiR$_3$, with the radicals R and R'' being as above defined, and again with the proviso that two radicals R may together form a single divalent radical.

Exemplary of the silylureas, the following are representative:

(i) N-Methyl-N-trimethylsilyl-N'-methyl-N'-butylurea;
(ii) N-Trimethylsilyl-N-methyl-N',N'-dimethylurea;
(iii) N-Trimethylsilyl-N-ethyl-N',N'-dimethylurea; and
(iv) N-Trimethylsilyl-N-butyl-N'-butyl-N'-trimethylsilylurea.

The compound containing an aminosilyl group will be a silazane when n is equal to 1 and when R' denotes an SiR$_3$ group.

The silazanes may be symmetrical or unsymmetrical; symmetrical disilazanes, in which the two SiR$_3$ groups are identical, are the preferred.

Exemplary of the disilazanes, the following are representative:

(i) Hexamethyldisilazane;
(ii) Heptamethyldisilazane;
(iii) 1,3-Diethyl-1,1,3,3-tetramethyldisilazane;
(iv) 1,3-Divinyl-1,1,3,3-tetramethyldisilazane;
(v) Hexaethyldisilazane; and
(vi) 1,3-Diphenyl-1,1,3,3-tetramethyldisilazane.

Lastly, hexamethyldisilazane and heptamethyldisilazane, which are found to be especially advantageous as catalysts, are the preferred from among the disilazanes.

The process of the present invention is useful for the cyclotrimerization, to a polyisocyanurate-polyisocyanate, of any simple or adduct polyisocyanate which is ether aliphatic, alicyclic or aromatic in nature, provided that the compound containing a aminosilyl group which is suitable for this reaction is properly selected as the catalyst.

Thus, the catalytic cyclotrimerization of simple or adduct polyisocyanates in which the isocyanate groups are not directly bonded to an aromatic nucleus may be readily carried out by using an aminosilane, a diaminosilane, a silylurea, or a silazane, such as defined above, as a catalyst.

In this respect, the following are representative of such aliphatic or alicyclic diisocyanates:

(i) Tetramethylene diisocyanate;
(ii) Pentamethylene diisocyanate;
(iii) Hexamethylene diisocyanate;
(iv) 1,2-Diisocyanatocyclohexane;
(v) 1,4-Diisocyanatocyclohexane;
(vi) 1,2-Bis(isocyanatomethyl)cyclobutane;
(vii) Bis(4-isocyanatocyclohexyl)methane; and
(viii) 3,3,5-Trimethyl-5-isocyanatomethyl-1-isocyanatocyclohexane.

Among these, hexamethylene diisocyanate is the preferred.

Lastly, among the adduct or prepolymer polyisocyanates which can be used as polyisocyanates of aliphatic type, exemplary are the modified polyisocyanates obtained by reacting an excess of an aliphatic or alicyclic polyisocyanate with a compound containing at least two groups which are reactive with isocyanate groups, such as a diamine or a diacid. The modified polyisocyanates, which may be mixed with simple polyisocyanates, may contain urea, biuret, ester or siloxane groups.

The process of the present invention can also be used for arresting the cyclotrimerization of any simple or adduct aromatic polyisocyanate into a polyisocyanurate-polyisocyanate, that is to say, those species in which the NCO group is directly bonded to an aromatic group. To achieve this, aminosilanes, diaminosilanes or silylureas such as defined above will be used as catalysts containing aminosilyl groups.

Exemplary of the aromatic diisocyanates which advantageously are used, the following are representative:

(i) 1,4-Diisocyanatobenzene;
(ii) 2,4- and 2,6-Diisocyanatotoluene (or their mixtures);
(iii) 4,4'-Diisocyanatodiphenylmethane;
(iv) 4,4'-Diisocyanatodiphenyl ether; and
(v) Polymethylene and polyphenylene polyisocyanates.

It is also possible to use, as an aromatic polyisocyanate, any adduct polyisocyanate produced by the polycondensation of an excess of a polyisocyanate with a polyfunctional compound such as a diamine, or a diacid. The modified polyisocyanates, which may be mixed with simple polyisocyanates, may contain urea, biuret, ester or siloxane groups.

The amount of catalytic agent added to the isocyanate can vary; expressed on a weight basis relative to the isocyanate employed, it usually ranges from 0.1 to 10% and preferably from 0.5 to 5%; small additional amounts of catalyst may be added during the reaction itself if appropriate.

The process of cyclotrimerization into a polyisocyanurate-polyisocyanate may be carried out by simply heating the reactants to a temperature which typically ranges from 50° C. to 180° C., preferably from 80° C., to 130° C., and usually around 100° C.

Where applicable, the cyclotrimerization reaction can also be carried out in a solvent medium, the latter being capable of being a low-polarity solvent such as, for example, an aliphatic or aromatic hydrocarbon, or an ester or an ether. The catalyst can then be added to the solvent and this solution can be added to the isocyanate. The catalyst solution can, of course, also be added to the isocyanate. Advantageously, the process is carried out in the absence of solvent.

When the isocyanurate content reaches the required value, an appropriate amount of water is added, if need be after the temperature of the trimerization mixture has been adjusted to selected value.

The excess polyisocyanate monomer can then be removed, if appropriate, by any known means, to obtain a polyisocyanurate-polyisocyanate having an extremely low content of isocyanate monomer, together with a low content of isocyanate dimer.

The polyisocyanurate-polyisocyanates, such as those produced from hexamethylene diisocyanate, are well-known compounds and are of particular interest as basic components of varnishes and paints.

In order to further illustrate the present invention and the advantages thereof, the following specific examples are given, it being understood that same are intended only as illustrative and in nowise limitative.

EXAMPLE 1

1600 g of 1,6-diisocyanatohexane, i.e., 9.5 moles, were charged into a 3-l round-bottomed flask fitted with a stirrer and a thermometer. This material was heated in an oil bath at 100° and 16 g (0.1 mole) of hexamethyldisilazane were added; the mixture was then heated to 120° C. and this temperature was maintained for 2 hr, 30 min. After this period of time, the mixture was cooled to 50° C. and the NCO group content was determined, and found to be 0.973 group/100 g.

0.9 g of water (0.05 mole) was then added, under good stirring and the mixture was maintained for 10 to 15 minutes under these conditions.

A fraction of the final mixture was sampled and maintained at 100° C. for 20 hours; after this period it was determined that the NCO content had not changed, evidencing that the trimerization reaction had been shortstopped, as intended.

The remaining reaction mixture was evaporated down under vacuum by means of a moving thin-film evaporator, until a residual content of free diisocyanate which did not exceed 0.1% was obtained. After one month of storage at 60° C., this content remained essentially unchanged (below 0.2%).

EXAMPLE 2

The reaction was the same as in Example 1, and carried out under the same conditions; after being cooled to 50°, the reaction mixture was divided into two equal parts:

(a) 0.05 mole of water (i.e., 1 mole per mole of catalyst) was added to the first half, and stirring was continued for 15 minutes;

(b) 0.0125 mole of water (i.e., 0.25 mole per mole of catalyst) was added to the second half, and stirring was continued for 15 minutes.

A fraction of each of these product mixtures was sampled and maintained at 100° for 20 hours; in both cases the NCO content remained unchanged.

The remainder of both reaction mixtures was evaporated down under vacuum by means of a moving film evaporator until a residual free diisocyanate content which did not exceed 0.1% by weight was obtained.

After one month of storage at 60°, this content remained essentially unchanged in product (a) and exceeded 0.2% by a small amount in product (b).

EXAMPLE 3

1600 g (9.5 moles) of 1,6-diisocyanatohexane were charged into a 3-liter round-bottomed flask. The latter was heated in an oilbath at 100° C. and 14.5 g (0.1 mole) of N,N'-diethylaminotrimethylsilane were added; the mixture was maintained at 100° for 3 hours and was then cooled to about 50°. The NCO content was then 0.951 group/100 g.

0.9 g (0.05 mole) of water was then added under good stirring and the mixture was maintained for 20 minutes under these conditions.

As in Example 1, after 20 hours at 100° the NCO content was found to be stable (content unchanged).

Similarly, the reaction mixture was evaporated down and the free diisocyanate content showed practically no variation after one month of storage at 60°.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a storage-stable polyisocyanurate-polyisocyanate, comprising catalytically cyclotrimerizing an aliphatic or cycloaliphatic polyisocyanate in the presence of a catalytically effective amount of an aminosilyl catalyst, and further comprising terminating the cyclotrimenization reaction when a predetermined desired amount of isocyanurate groups has been reached, by adding to the reaction mixture a reaction terminating amount of water.

2. The process as defined by claim 1, comprising adding from about 0.25 to 1 mole of water per aminosilyl group comprising said catalyst.

3. The process as defined by claim 2 comprising adding from about 0.4 to 0.8 mole of water per aminosilyl group comprising said catalyst.

4. The process as defined by claim 1, comprising adding said water at a temperature ranging from about 0° to 100° C.

5. The process as defined by claim 4, comprising adding said water at a temperature ranging from about 15° to 60° C.

6. The process as defined by claim 1, said catalytically effective amount ranging from about 0.1 to 10% by weight, relative to said polyisocyanate.

7. The process as defined by claim 1, carried out in an inert, low-polarity solvent medium.

8. The process as defined by claim 1, said aminosilyl catalyst having the formula:

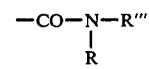

wherein R is an aliphatic or cycloaliphatic, saturated or unsaturated monovalent hydrocarbon radical, an aryl, aralkyl or alkylaryl radical, or a halogen or CN substituted such radical, with the proviso that any two of the radicals R may together form a single divalent hydrocarbon radical; R' is a monovalent radical R or SiR$_3$ or an amide radical having the formula:

$$-CO-N-R'''$$
$$\phantom{-CO-N-}|$$
$$\phantom{-CO-N-}R$$

in which R''' is R or SiR$_3$, with the proviso that R', when neither an amide nor SiR$_3$, may together form with R''' a single divalent hydrocarbon radical; R'' is R, or a hydrogen atom if R' is not an amide; and D is the integer 1 or 2, with the proviso that if n is 2, R' is R.

9. The process as defined by claim 8, wherein said aminosilyl catalyst having the formula (I), R is an alkyl, alkenyl, haloalkyl or haloalkenyl radical having from 1 to 5 carbon atoms, and optionally comprising from 1 to 6 chlorine and/or fluorine substituents, a cycloalkyl, cycloalkenyl, halocycloalkyl or halocycloalkenyl radical having from 3 to 8 carbon atoms, and optionally comprising from 1 to 4 chlorine and/or fluorine substituents, an aryl, alkylaryl or haloaryl radical having from 6 to 8 carbon atoms, and optionally comprising from 1 to 4 chlorine and/or fluorine substituents, or a cyanoalkyl radical having from 3 to 4 carbon atoms; two of the radicals R borne by the same silicon atom may together form a single divalent radical having from 1 to 4 carbon atoms; R' is R, SiR$_3$ or —CO(NR)—R''', with R''' being R or SiR$_3$, with the proviso that R' may together form with R'' a single alkylene radical having from 4 to 6 carbon atoms; and R'' is an alkyl or alkenyl radical having from 1 to 4 carbon atoms, a cycloalkyl or cycloalkenyl radical having from 4 to 6 nuclear carbon atoms, a phenyl, tolyl or xylyl radical, or hydrogen if R' is not an amide.

10. The process as defined by claim 8, wherein said aminosilyl catalyst is an aminosilane.

11. The process as defined by claim 8, wherein said aminosilyl catalyst is a diaminosilane.

12. The process as defined by claim 8, wherein said aminosilyl catalyst is a silylurea.

13. The process as defined by claim 8, wherein said aminosilyl catalyst is a silazane.

14. The product of the process as defined by claim 1.